(12) United States Patent
Gold et al.

(10) Patent No.: US 6,730,482 B2
(45) Date of Patent: May 4, 2004

(54) MODIFIED SELEX PROCESSES WITHOUT PURIFIED PROTEIN

(75) Inventors: Larry Gold, Boulder, CO (US); Dominic A. Zichi, Boulder, CO (US); Jonathan Drew Smith, Bouler, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 10/096,641

(22) Filed: Mar. 12, 2002

(65) Prior Publication Data

US 2003/0044818 A1 Mar. 6, 2003

Related U.S. Application Data

(63) Continuation of application No. 09/668,602, filed on Sep. 22, 2000, now Pat. No. 6,376,190.

(51) Int. Cl.$^7$ .................................................. C12Q 1/68
(52) U.S. Cl. ........................ 435/6; 435/7.1; 435/7.8; 435/40.5; 435/40.51; 536/23.1; 536/25.4; 436/501; 436/503
(58) Field of Search ............................ 435/6, 7.8, 40.5, 435/40.51; 536/23.1, 25.4; 436/501, 503; 5/7.1

(56) References Cited

U.S. PATENT DOCUMENTS

| | | | |
|---|---|---|---|
| 5,270,163 A | | 12/1993 | Gold et al. |
| 5,475,096 A | | 12/1995 | Gold et al. |
| 5,496,938 A | | 3/1996 | Gold et al. |
| 5,567,588 A | | 10/1996 | Gold et al. |
| 5,580,737 A | | 12/1996 | Polisky et al. |
| 5,596,079 A | | 1/1997 | Smith et al. |
| 5,637,459 A | | 6/1997 | Burke et al. |
| 5,660,985 A | | 8/1997 | Pieken et al. |
| 5,683,867 A | | 11/1997 | Biesecker et al. |
| 5,705,337 A | | 1/1998 | Gold et al. |
| 5,707,796 A | | 1/1998 | Gold et al. |
| 5,723,323 A | | 3/1998 | Kauffman et al. |
| 5,763,177 A | | 6/1998 | Gold et al. |
| 5,789,157 A | * | 8/1998 | Jensen et al. |
| 5,864,026 A | * | 1/1999 | Jensen et al. |
| 5,976,821 A | | 11/1999 | Huston et al. |
| 6,001,577 A | | 12/1999 | Gold et al. |
| 6,011,020 A | | 1/2000 | Gold et al. |
| 6,376,190 B1 | * | 4/2002 | Gold et al. |

FOREIGN PATENT DOCUMENTS

| | | |
|---|---|---|
| UA | 2 183 661 | 6/1987 |
| WO | WO 89/06694 | 7/1989 |
| WO | WO 91/19813 | 12/1991 |
| WO | 92/14843 * | 9/1992 |
| WO | WO 99/31275 | 6/1999 |

OTHER PUBLICATIONS

Ellington & Szostak (1990) *Abstract Presented at RNA Processing Meeting* p. 84.
Joyce (1989) *Gene* 82:83–87.
Joyce & Inoue (1989) *Nucleic Acids Research* 17:711–722.
Kinzler & Vogelstein (1989) *Nucleic Acids Research* 17(10):3645–3653.
Kramer, et al. (1974) *J. Mol. Biol.* 89:719–736.
Levisohn & Spiegel (1986) *Proc. Natl. Acad. Sci. USA* 60:866–872.
Levinsohn & Spiegelman (1969) *Proc. Natl. Acad. Sci. USA* 63:805–811.
Nieuwlandt, et al. (1995) *Biochemistry* 34:5651–5659.
Oliphant & Struhl (1987) *Methods in Enzymology* 155:568–582.
Oliphant & Struhl (1988) *Nucleic Acids Research* 16:7673–7683.
Oliphant, et al. (1986) *Gene* 44:177–183.
Oliphant, et al., (1989) *Mol. Cell. Biol.* 9:2944–2949.
Robertson & Joyce (1990) *Nature* 344:467–468.
Stanfield, et al. (1990) *Science* 248:712–719.
Szostak (1988) *Redesigning the Molecules of Life* pp. 87–113.
Thiesen & Bach (1990) *Nucleic Acids Research* 18:3203–3208.
Xu & Ellington (1996) *Proc. Natl. Acad Sci. USA* 93:7475–7480.

* cited by examiner

Primary Examiner—BJ Forman
(74) Attorney, Agent, or Firm—Swanson & Bratschun, LLC

(57) ABSTRACT

This invention is directed towards a method for obtaining nucleic acid ligands against target proteins without directly purifying the target proteins. The method used in the invention is called SELEX, which is an acronym for Systematic Evolution of Ligands by EXponential enrichment. The nucleic acid ligands of the invention are useful as diagnostic and therapeutic agents for diseases in which the targets proteins play a causative role.

5 Claims, No Drawings

MODIFIED SELEX PROCESSES WITHOUT PURIFIED PROTEIN

CROSS REFERENCE TO RELATED APPLICATIONS

This application is a continuation of U.S. patent application Ser. No. 09/668,602, filed Sep. 22, 2000 now U.S. Pat. No. 6,376,190 entitled "Modified SELEX Processes Without Purified Protein."

FIELD OF THE INVENTION

This invention is directed toward a method for obtaining nucleic acid ligands against target proteins without directly purifying the target proteins. The method used in the invention is called the SELEX process, which is an acronym for Systematic Evolution of Ligands by EXponential enrichment.

BACKGROUND OF THE INVENTION

The past ten years have seen phenomenal advances in the characterization of the genomes of many species. Indeed, the human genome sequence—encoding for approximately 100,000 proteins—is now substantially complete. With the completion of a genome sequence, the linear amino acid sequences of all the proteins potentially encoded by that genome are known. The goal of the biomedical research community is to use the genomic data to learn about the functions of the proteins that are encoded by the genome, and then determine the role that these proteins play in pathogenesis and disease. Unfortunately, the tools for identifying the function of proteins—their structural or enzymatic activities, and their level of synthesis—are dramatically less well developed than those for determining genomic sequences. As a result, the characterization of the functions of such proteins is the rate limiting step in the exploitation of genomic data for the development of new diagnostic and therapeutic agents.

Although some proteins are identified solely through the existence of their coding sequence in the genome, more functional approaches to protein identification and characterization have been devised. For example, one approach involves isolating all the proteins that are expressed under predetermined conditions in a certain tissue, then resolving those proteins from one another by electrophoresis on a 2-dimensional gel. Following separation, individual protein "spots" on the gel are picked and proteolytically-digested to yield peptides. The resulting peptides can be analyzed by reiterative mass spectrometry in order to determine their (partial) linear amino acid sequences. Finally, the amino acid sequences of the peptides are used to search genomic or cDNA sequences in order to obtain the DNA sequence that encodes the protein from which the peptide was derived. In this way, it is possible to prepare protein and gene expression profiles. However, because this approach is extremely labor and capital-intensive—requiring several days to analyze a single gel—it is not suited to high-throughput, routine diagnostic applications.

Regardless of the manner in which a protein implicated in disease is initially identified, it is ultimately crucial to obtain ligands to that protein, because such ligands can serve as therapeutic or diagnostic reagents. In order to generate ligands, it is necessary to have a purified source of the protein. However, because important proteins are often present in vanishingly-small amounts in biological tissues, purification—if it is even possible at all—is often a costly, labor-intensive, and time-consuming procedure. Expression of proteins is also fraught will difficulties, often because of the complexity of the post-translational modifications seen in mammalian proteins. Because of these difficulties, there is a need in the field of functional genomics for a method of generating ligands of target proteins without first requiring that the target protein be directly purified.

There have been several attempts in the art to overcome these difficulties by generating ligands of synthetic peptides with the same linear amino acid sequence as a portion of the target protein. The hope in this approach is that the ligand—typically an antibody—to the peptide will recognize the same peptide in the natural context of the intact protein. There are two fundamental problems with this approach. First, because protein structures have a large internal mass compared to their external surface, most peptide sequences from a specific protein lie within the internal mass of the protein and are not exposed to solvent. As a result, many ligands to peptides will not be able to access the same peptides within the intact protein. Second, isolated peptides typically have random, undefined structures, whereas the same peptide in the intact protein will have one or a few defined structures as a result of intra-molecular constraints imposed upon it. Because ligands are generated using the isolated peptide as the target, many ligands will not recognize the defined peptide structure within the intact protein. Both of these problems cause anti-peptide antibodies to have weak affinities for the proteins that contain the same peptides.

A new class of non-protein-based ligands is found in nucleic acid molecules. The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", U.S. Pat. No. 5,270,163 (see also WO 91/19813) entitled "Nucleic Acid Ligands" each of which is specifically incorporated by reference herein. Each of these patents and applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, and U.S. patent application Ser. No. 08/443,959 filed May 18, 1995, both entitled "Photoselection of Nucleic Acid Ligands," and both now abandoned, and U.S. Pat. No. 5,763,177, U.S. Pat. No. 6,001,577, U.S. patent application Ser. No. 09/459,553, filed Dec. 13, 1999, and U.S. patent application Ser. No. 09/619,213, filed Jul. 17, 2000, each of which is entitled "Systematic Evolution of Nucleic Acid Ligands by Exponential Enrichment: Photoselection of Nucleic Acid Ligands and Solution SELEX," all describe a SELEX based method for selecting nucleic acid ligands containing photoreactive groups capable of binding and/or photocrosslinking to and/or photoinactivating a target molecule. These patents and patent applications are referred to in this application collectively as "the photo SELEX process applications."

U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. Pat. No. 6,011,020 entitled "Nucleic Acid Complexes".

The SELEX process has been adapted in order to allow the high-throughput, automated generation of high affinity nucleic acid ligands to targets of interest. Methods and apparatus for automated generation of nucleic acid ligands are described in U.S. patent application Ser. No. 09/232,946, filed Jan. 19, 1999, U.S. patent application Ser. No. 09/356, 233 filed Jul. 16, 1999, and U.S. patent application Ser. No. 09/616,284, filed Jul. 14, 2000, each of which is entitled "Methods and Apparatus for the Automated Generation of Nucleic Acid Ligands." We refer to these patent applications collectively as "the automated SELEX process applications."

Nucleic acid ligands may be attached to the surface of solid supports to form microarrays. Such microarrays (also commonly referred to as "biochips"), and methods for their manufacture and use, are described in U.S. patent application Ser. No. 08/990,436, filed Dec. 15, 1997, U.S. patent application Ser. No. 08/211,680, filed Dec. 14, 1998, now abandoned, Patent Cooperation Treaty Application Serial No. PCT/US98/26515, filed Dec. 14, 1998, U.S. patent application Ser. No. 09/581,465, filed Jun. 12, 2000, each of which is entitled "Nucleic Acid Ligand Diagnostic Biochip." We refer to these patent applications collectively as "the biochip applications."

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 9, 1993, now abandoned, and U.S. Pat. No. 5,660,985, both entitled "High Affinity Nucleic Acid Ligands Containing Modified Nucleotides", and U.S. patent application Ser. No. 09/362,578 filed Jul. 28, 1999, entitled "Transcription-free SELEX", each of which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are DNA molecules that are modified with a photoreactive group on 5-position of pyrimidine residues. The modifications can be pre- or post-SELEX process modifications.

Each of the above described patent applications, many of which describe modifications of the basic SELEX procedure, are specifically incorporated by reference herein in their entirety.

There are a number of prior art teachings of nucleic acid ligands to unconstrained peptides. For example, Nieuwlandt et al, *Biochemistry* 34: 5651–5659 (1995) describe a high-affinity (190 nm $K_d$) nucleic acid ligand to the 11 amino acid tachykinin substance P. Ellington and Xu, *Proc. Natl. Acad. Sci. USA*, 93: 7475–7480 (1996), teach that a nucleic acid ligand to a 17-mer peptide fragment of Human Immunodeficiency Virus (HIV) Rev protein can bind specifically to the same peptide within intact Rev protein. However, because of the aforementioned problems, the affinity of the nucleic acid ligand for the isolated 17-mer peptide is significantly better than for the intact Rev protein i.e., the $K_d$ for the peptide is lower than the $K_d$ for the intact protein.

The present invention provides for the first time a method for obtaining nucleic acid ligands that bind to target proteins without requiring a source of purified target protein.

SUMMARY OF THE INVENTION

The methods provided herein use the SELEX process for ligand generation. In particular, the methods of the instant invention allow the generation of nucleic acid ligands to protein targets that are not generally available in purified form, but for which a least a partial cDNA or genomic sequence is known. The nucleic acid ligands of the instant invention are initially generated by the SELEX process, using, as SELEX targets, peptides corresponding in sequence to the target protein, or derivatives of target proteins (including fragments of target proteins) expressed in vitro or in vivo. This method generates candidate nucleic acid mixtures that are enriched for nucleic acid ligands with affinity to the peptide or expressed protein. Further enrichment of the candidate mixture for those nucleic acid ligands that also have affinity for the intact, native target protein may optionally be achieved by performing an additional number of rounds of the SELEX process using, as a SELEX target, a complex mixture suspected of containing the target protein e.g., a tissue extract or biological fluid. Although such complex mixtures may contain many other proteins, and may contain only minute quantities of the target protein, the initial enrichment performed using the peptide or expressed protein as a SELEX target nevertheless allows high affinity nucleic acid ligands of the target protein to be obtained.

Nucleic acid ligands generated according to the methods of the instant invention will have a great utility as diagnostic and prognostic reagents, as novel therapeutics, and as agents for the identification of novel therapeutic targets.

DETAILED DESCRIPTION OF THE PREFERRED EMBODIMENTS

The central method utilized herein for identifying nucleic acid ligands to proteins which are not readily available in purified form is called the SELEX process, an acronym for Systematic Evolution of Ligands by Exponential enrichment.

Definitions

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers". The term aptamer is used interchangeably with nucleic acid ligand throughout this application. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. In the present invention, the targets include peptides and polypeptide molecules. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most favorably with the target from a pool which contains a very large number of nucleic acids. Cycling of the selection/amplification procedure is continued until a selected goal is achieved. In the present invention, the SELEX methodology is employed to obtain nucleic acid ligands to proteins without first directly purifying the protein target.

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX targets include synthetic peptides and polypeptides comprising a linear sequence of amino acids based on the genomic or cDNA sequence of a protein, particularly one that is not readily available in purified form. The SELEX targets of the instant invention also include the intact cognate proteins corresponding to said peptides, wherein said intact cognate protein is contained within a complex mixture or preparation, including, but not limited to, serum and other biological fluids, tissue culture medium, and tissue extracts and homogenates. The SELEX targets of the instant invention further include proteins or peptides expressed in vivo and in vitro.

As used herein, "peptide" is defined as a relatively short contiguous stretch of amino acids—either naturally occurring amino acids or synthetic amino acids—linked through a peptide backbone. Preferably, the peptides used in the instant invention are between 4 and 100 amino acids in length, most preferably between 4 and 40 amino acids in length. In some embodiments of the invention, the linear amino acid sequence of a peptide is predicted by a contiguous stretch of nucleotides in a gene or cDNA sequence.

As used herein, "solid support" is defined as any surface to which molecules may be attached through either covalent or non-covalent bonds. This includes, but is not limited to, membranes, microtiter plates, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

As used herein, "biological fluid" refers to any biological substance, including but not limited to, blood (including whole blood, leukocytes prepared by lysis of red blood cells, peripheral blood mononuclear cells, plasma, and serum), sputum, urine, semen, cerebrospinal fluid, bronchial aspirate, sweat, feces, synovial fluid, macerated tissue, and tissue extracts. Biological fluid typically contains cells and their associated molecules, soluble factors, small molecules and other substances.

As used herein, "tissue" refers to a collection of cells that act together to form a particular structure or perform a particular function. Examples of tissues include, but are not limited to, skin, liver, kidney, muscle, and blood.

As used herein, "complex mixture" refers to a preparation known to comprise, or strongly suspected of comprising, a SELEX target. Complex mixtures include, but are not limited to, biological fluids, tissues, and partially purified preparations of the target.

Note that throughout this application, various references are cited. Every reference cited herein is specifically incorporated in its entirety.

A. The SELEX Process Methodology

In the preferred embodiment, the nucleic acid ligands of the present invention are derived from the SELEX process methodology. The SELEX process is described in U.S. patent application Ser. No. 07/536,428, entitled "Systematic Evolution of Ligands by Exponential Enrichment," now abandoned, U.S. Pat. No. 5,475,096 entitled "Nucleic Acid Ligands," and in U.S. Pat. No. 5,270,163 (see also WO 91/19813) entitled "Nucleic Acid Ligands." These applications, each specifically incorporated herein by reference, are collectively called the SELEX Patent Applications.

The SELEX process provides a class of products which are nucleic acid molecules, each having a unique sequence, and each of which has the property of binding specifically to a desired target compound or molecule. Target molecules are preferably proteins (as in this application), but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are chosen either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

Many modifications of the basic SELEX process are enabled by those patent applications and patents referred to within the "Background of the Invention." Other modifications are known to one of ordinary skill in the art. Such modifications may be made post-SELEX process (modification of previously identified unmodified ligands) or by incorporation into the SELEX process.

B. Modified SELEX Processes Using Peptides as Initial Targets

In its broadest aspect, the present invention provides adaptations of the SELEX process that allow the generation of nucleic acid ligands of a protein target for which at least a partial genomic or cDNA sequence is known, without first directly purifying the protein target. Some such target proteins are identified solely from the existence of a coding sequence in a genome or in a cDNA library. Other target proteins with at least partially known amino acid sequences cannot be purified to sufficient homogeneity, or in sufficient quantities, to serve as targets for ligand generation, either by the traditional SELEX procedures outlined above or through other techniques. For example, this includes proteins that are identified initially through mass-spectroscopic analysis of a protein expression profile.

In one series of embodiments, the SELEX process is initially performed using a synthetic peptide as the SELEX target. Preferably, the peptide sequence chosen is one that has a strong likelihood of residing on the external surface of the native target protein. The determination of which peptide sequences in a protein are exposed to solvent can be achieved by a number of techniques well known in the art. For example, a hydrophobicity plot can be used: strongly hydrophilic sequences are more likely to reside on the exterior of the protein than hydrophobic sequences. In addition, if the target protein of interest has a homologue with a known three-dimensional structure (e.g., determined through X-ray diffraction or nuclear magnetic resonance), it is possible to predict which amino acids in the target protein lie on the external surface. The invention expressly contemplates the combination of a number of different computational techniques in order to make such structural predictions, including, but not limited to, sequence alignment, secondary structure prediction, and protein sequence fold recognition (threading peptide sequences through known three-dimensional structures).

In preferred embodiments, the peptide sequence will be a linear subsequence of the target protein. In other embodiments, peptide sequences will comprise short linear sequences of the target protein that are combined to yield a group of surface residues thought to be spatially contiguous in the target protein from structural or modeling data. Such peptide sequences will not be linearly contiguous in the target protein sequence but may provide better peptide targets closer to conformationally accessible residues in the intact native protein.

In preferred embodiments, a predetermined number of rounds of the SELEX process are performed using the peptide as a target, leading to the formation of a candidate nucleic acid mixture enriched for nucleic acid ligands to the peptide. Without being limited to a single theory, it is believed that at least some nucleic acid ligands in this situation can bind to the isolated peptide—which frequently will be unstructured in solution, populating many conformations—and force it to adopt a particular structural conformation. Different nucleic acid ligands may induce different peptide conformations with potentially different binding free energies. This phenomenon is known as "conformational fit" or "induced fit," and has been previously described for anti-peptide antibodies, and nucleic acid ligands, as described in Stanfield et al, Science 248: 712–719 (1990), and in Xu & Ellington, Proc. Natl. Acad. Sci. USA, 93: 7475–7480 (1996). In essence, performing the SELEX process as described herein using a peptide will provide a candidate mixture that is enriched for nucleic acid ligands that induce the conformationally unconstrained peptide to adopt a variety of distinct binding conformations.

In possible contrast to the isolated peptide, the same peptide in the intact target protein will be conformationally-constrained by its interaction with other amino acids in the same protein, and so will adopt only one, or perhaps several, of these possible conformations. Therefore, it is preferable to further enrich the initial enriched candidate mixture for those nucleic acid ligands that recognize the peptide conformation(s) that exists in the intact target protein. In preferred embodiments, this is done by performing an additional number of rounds of the SELEX process using the initial enriched candidate mixture and, as the SELEX target, a complex mixture suspected of comprising, or known to comprise, the target protein. Suitable complex mixtures include, but are not limited to, extracts of biological tissue, a biological fluid such as serum or urine, and partially purified isolates of the intact target protein. Nucleic acid ligands in the initial enriched candidate mixture that can bind to an isolated peptide and induce it to adopt a conformation that is either the same or closely similar to the conformation of the same peptide within the intact target protein will bind to the intact target protein in the complex mixture. Indeed, it is likely that such nucleic acid ligands will actually have a lower $K_d$ (higher affinity) for the intact protein than for the isolated peptide. This is primarily because the peptide within the intact protein is constrained, and hence need not be induced into a particular conformation by the nucleic acid ligand (an energetically costly process). As a result, these nucleic acid ligands will be enriched by the final SELEX process rounds relative to nucleic acid ligands that bind to the peptide in conformations other than the native one. Nucleic acid ligands that bind to other components of the complex mixture (e.g., to other serum proteins) are poorly represented in the initial enriched candidate nucleic acid mixture due to the initial selection using the peptide as the SELEX target. In preferred embodiments, only a limited number of rounds of the SELEX process are performed using the complex mixture—e.g., 1 or 2 rounds—to prevent such poorly represented nucleic acid ligands from becoming more dominant.

In preferred embodiments, the number of rounds of the SELEX process used at each point—e.g., the number of rounds using the peptide as a SELEX target, and the number of rounds using the target protein contained within the complex mixture as a SELEX target—is optimized in order to yield nucleic acid ligands with the desired affinity for the intact target protein. Determination of the number of rounds is routine experimentation for one skilled in the art. By way of example only, in some embodiments 2–10 rounds may be performed using the peptide as a SELEX target followed by a few rounds using the target protein contained within the complex mixture.

In some embodiments, the methods provided herein are used to generate nucleic acid ligands to a protein (with at least a partially known amino acid sequence) that is available in purified form, but not in sufficient quantities or purities to permit a traditional SELEX process experiment to be carried out economically. In this embodiment, the SELEX process is carried out for a predetermined number of rounds using a peptide as a target, thereby yielding an initial enriched candidate mixture. Then, the final rounds of the SELEX process are carried out using the purified protein. Because an enriched candidate mixture is used for these final rounds, only a very small amount of the purified protein is required to generate high affinity nucleic acid ligands.

As an alternative to using a complex mixture as the SELEX target in the final rounds of the SELEX process, in some embodiments bacteriophage displaying the target protein on their exterior surfaces are used. Phage display technology is discussed in some detail in the section below entitled "The SELEX Process Using Proteins or Peptides Expressed by Cells or Displayed on Phage."

In preferred embodiments, the modified SELEX process is initially carried out using peptide attached to a solid support. A candidate mixture of single stranded nucleic acid molecules is then contacted with the solid support. After incubation for a predetermined time at a selected temperature, the solid support is washed to remove unbound candidate nucleic acid ligand. The nucleic acid ligands that bind to the peptide are released into solution, then reverse transcribed by reverse transcriptase and amplified using the Polymerase Chain Reaction. The amplified candidate mixture is then used to begin the next round of the SELEX process using the peptide as the target. After a predetermined number of rounds using the peptide as a target, an initial enriched candidate mixture is obtained. The final round(s) of the SELEX process can then be carried out by performing the same process, using a solid support onto which a complex mixture has been adsorbed instead of the peptide.

In the above embodiments, the solid support can be a nitrocellulose filter. Nucleic acids in the candidate mixture that do not interact with the immobilized protein in the complex mixture/peptide can be removed from this nitrocellulose filter by application of a vacuum. In other embodiments, the target is adsorbed on a dry nitrocellulose filter, and nucleic acids in the candidate mixture that do not bind to the peptide/protein are removed by washing in buffer. In further embodiments, the solid support is a microtiter plate comprised of, for example, polystyrene. In still further embodiments, the solid support is a micron sized bead, either paramagnetic or not.

In especially preferred embodiments, the methods of the instant invention are combined with the methods of the aforementioned photo SELEX process applications to obtain nucleic acid ligands with photoreactive groups that photocrosslink to both the peptide and the intact target protein. Any modified nucleotide residue that is capable of photocrosslinking (or chemically reacting) with a target molecule, such as 5-BrdU, 5-Br U, 5-IdU, 5-IU, 5-benzophenone dU, 5-benzophenone U, or other 5-modified nucleotides, can be incorporated into the candidate mixture and may be useful in this application. In preferred embodiments, the crosslinking occurs when 5-bromo-deoxyuracil (5-BrdU) residues incorporated into a nucleic acid ligand are irradiated with ultraviolet (UV) light. In these embodiments, the BrdU residues become covalently attached to tyrosine or other electron-rich amino acid residues. Hence, in designing the peptide sequence for the initial SELEX rounds, it is preferable to choose a sequence that contains at least one tyrosine or other electron-rich amino acid residue.

C. The SELEX Process Using Proteins or Peptides Expressed by Cells or Displayed on Phage In further embodiments of the invention, the target protein (or a fragment thereof, such as a peptide) is produced within an in vivo or in vitro expression system. The SELEX process, or the photo SELEX process, is then performed as outlined above using the expressed target protein. The basic principle is the same as in the proceeding embodiments: performing SELEX against expressed target protein (or fragments thereof) will yield a candidate mixture of nucleic acids enriched for nucleic acid ligands that have affinity for the expressed target protein. If short fragments of the target protein are expressed, then it is likely that these fragments will not have a defined structure in isolation, for the same reasons as given above in the peptide SELEX embodiments. In this case, some of the nucleic acid ligands in the enriched candidate mixture will likely induce the expressed fragment to adopt the same conformation as in the native, intact target protein. If long fragments are expressed, then these are more likely to adopt the same conformation in isolation as within the intact native protein. In this case, some of the nucleic acid ligands in the enriched candidate mixture will have affinity for both the expressed fragment and the same fragment within the native intact target protein. In either case, in order to further enrich for the nucleic acid ligands that bind to the native target protein (which may not be available in purified form, or is available only very sparingly), the enriched candidate nucleic acid mixture can then optionally be used to perform additional rounds of the SELEX process using a complex mixture suspected of containing the target protein as the SELEX process target. These methods, again, allow the generation of nucleic acid ligands to target proteins without a purified source of that target protein.

There are many ways known in the art to express proteins or fragments thereof in vitro or in vivo. One well known method is phage display. Phage display technology allows proteins or peptides to be expressed on the exterior surface of bacteriophages by fusing the coding sequence for the target protein or peptide to the bacteriophage coat protein coding sequence. Each phage displays multiple copies of the resulting fusion protein, and the DNA encoding the fusion protein is contained within the phage particle. Phage particles can then be screened for a desired activity mediated by the protein of interest expressed on their surface. Phage with the desired activity can be recovered, grown clonally in bacterial cells, and the protein responsible for the activity can be identified by analysis of the DNA sequence contained within the phage particle.

In some embodiments of the invention, the SELEX process is performed using display phage as a target. In one particular embodiment, phage are constructed that display a peptide or protein fragment corresponding in sequence to a target protein which is not available in purified form, but for which a cDNA or genomic sequence is at least partially known. As described above, the displayed peptide or protein fragment preferably has a strong likelihood of residing on the external surface of the native target protein. In strongly preferred embodiments, display phage are used as targets for a modification of the basic SELEX process known as the Counter-SELEX process. The Counter-SELEX process is described in great detail in U.S. Pat. No. 5,580,737. The Counter-SELEX process is used to remove from the enriched candidate mixture nucleic acid ligands with specific affinity for components of the display phage other than the displayed peptide. This is done in the Counter-SELEX process by performing a predetermined number of rounds of the SELEX process using "empty" phage that do not display the peptide as a Counter-SELEX target. In each such round of the Counter-SELEX process, nucleic acid ligands with specific affinity for the "empty" phage are discarded. The result of the counter-SELEX process is a candidate mixture enriched for nucleic acid ligands with affinity for the displayed peptide or protein, and depleted of nucleic acid ligands with affinity for other components of the phage. Again, as described above, the Counter-SELEX enriched candidate nucleic acid mixture can then optionally be used to perform an additional number of rounds SELEX process using as a target a complex mixture suspected of containing the target protein. Alternatively, the target for these optional additional rounds of the SELEX process can be phage displaying the intact protein.

In some embodiments, the Counter-SELEX process is performed using display phage associated with a solid support (e.g., a paramagnetic bead) as the SELEX target, and "empty" phage within the reaction buffer as the Counter-SELEX target. In this way, nucleic acid ligands with affinity for the peptide or protein fragment displayed by phage can be partitioned from nucleic acid ligands with affinity to other components of the phage simply by partitioning the solid support from the reaction buffer. This process can easily be automated, as described in great detail in the automated SELEX applications.

In other embodiments, rather than using a single phage clone as a SELEX or Counter-SELEX target, a phage display library is used. For example, a phage display library can be constructed from a cDNA library that represents all of the mRNA obtained from a particular tissue or biological fluid under predetermined conditions; alternatively, a cDNA library could represent randomized peptide coding sequences. By using such a phage display library as a SELEX process target and "empty" phage as a Counter-SELEX process target (discarding those nucleic acid ligands that have affinity for the "empty" phage), an enriched candidate mixture of nucleic acid ligands with increased affinity for the proteins or peptides encoded by the cDNA clones in the library is obtained. Preferably, additional rounds of the SELEX process are then performed using this enriched candidate mixture and, as a target, the particular tissue or biological fluid from which the mRNA was obtained. In this way, the enriched candidate mixture can be further enriched for those nucleic acid ligands that recognize both phage-displayed cDNA clones and also the corresponding intact target proteins in the tissue or biological fluid. The methods provided herein can be used, for example, to prepare a panel of nucleic acid ligands to all of the protein components expressed within a particular tissue under predetermined conditions.

In still further embodiments, the phage display method can be used to prepare panels of nucleic acid ligands to proteins targets that are expressed differentially e.g., in a tissue/biological fluid specific pattern; or in a diseased tissue but not in a healthy tissue; or in a particular tissue in response to certain conditions. This is done by combining the methods of the instant invention with differential phage display technology. For tissue specific panels, the following procedure may be followed. First, two phage display libraries are generated: a first library expressing cDNA from tissue A, and a second expressing cDNA from tissue B. Then, the Counter-SELEX process is performed using the first phage display library as a SELEX target, and the second phage display library as a Counter-SELEX target. Nucleic acid ligands in the candidate mixture that bind to the Counter-SELEX target are discarded. The resulting enriched nucleic acid candidate mixture from the Counter-SELEX process is optionally used to perform additional rounds of the SELEX process using a preparation—such as a crude homogenate, or an extract—of the first tissue as the SELEX target. The result is a candidate mixture of nucleic acids that is enriched for nucleic acid ligands to proteins expressed in tissue A but not in tissue B. The use of the second phage display library as a Counter-SELEX target serves the twin aims of depleting the candidate nucleic acid mixture of those nucleic acid ligands that bind to proteins that are expressed in both tissues A and B, and also of those nucleic acid ligands that bind to components of the display phage themselves.

Those skilled in the art will appreciate that many other permutations of the above embodiment are possible. The important variables are 1) choice of the Counter-SELEX process target; and 2) choice of the course of action to be taken with those nucleic acid ligands with affinity for the Counter-SELEX process target e.g., either discarding or keeping such nucleic acid ligands. As discussed above, if the SELEX target is associated with a solid support, and the Counter-SELEX target is within the reaction buffer, it is possible to partition nucleic acid ligands with specific affinity to the SELEX target from those with affinity to the Counter-SELEX process target simply by partitioning the solid support from the reaction buffer. For example, it is possible to select for nucleic acid ligands to proteins that are expressed in both tissue A and tissue B. This can be done by using the tissue B phage display library as a Counter-SELEX process target (discarding those nucleic acid ligands in the candidate mixture that do not bind to the tissue B phage display library). As a further example, the methods provided herein can be adapted to provide nucleic acid ligands to proteins that are expressed by a cancerous tissue, but not by a normal tissue. As yet a further example, this methodology can be used to obtain panels of nucleic acid ligands to proteins whose expression in a single tissue is responsive to predetermined conditions e.g. in response to the administration of a particular drug, such as a candidate therapeutic.

In other embodiments, the abovementioned methods may be combined with the methods provided in the photo SELEX process applications in order to obtain nucleic acid ligands that are capable of photocrosslinking to the target protein.

In still further embodiments, a target protein (or fragment thereof) with at least a partially known cDNA or genomic sequence is expressed in either a prokaryotic or a eukaryotic cell. Techniques for such expression are well known in the art. In general, a DNA sequence encoding for at least a portion of the target protein is fused downstream of a promoter that can control the expression of the target protein within the cell. The resulting construct is then introduced into cells—for example, by transfection for eukaryotic cells, or electroporation for prokaryotic cells—allowing the target protein, or fragments thereof, to be expressed under predetermined conditions. Furthermore, it is possible to express the target protein at particular sites in the cell—e.g., on the cell surface, or even secreted from the cell—by fusing the target protein coding sequence to a coding sequence that directs the resulting fusion protein to that site. In the present invention, cells expressing the target protein, or fractions of such cells, can then be used as targets for the SELEX process. Preferably, Counter-SELEX is performed, using cells that do not express the target protein as the Counter-SELEX process target, in order to deplete the candidate nucleic acid mixture of nucleic acid ligands with affinity for cell components other than the expressed target protein. The resulting enriched candidate nucleic acid mixture can then be used to perform an additional number of rounds of the SELEX process using, as a target, a complex mixture suspected of containing the intact target protein.

In other embodiments, a cDNA library—obtained from, for example, mRNA expressed in a particular tissue—is expressed within prokaryotic or eukaryotic cells, and the Counter-SELEX process is performed using the library-expressing cells as the SELEX target, and using the same cells without the cDNA library as the Counter-SELEX target. By discarding those nucleic acid ligands with affinity for the Counter-SELEX target, a candidate mixture is obtained that is enriched for nucleic acid ligands with affinity to expressed cDNA clones from the library. Preferably, an additional number of rounds of the SELEX process are then performed with this enriched candidate mixture using the biological material from which the cDNA library was obtained as a SELEX target.

In another aspect, the invention provides methods for obtaining panels of nucleic acid ligands to targets that are specific to certain tissues or biological fluids, or to targets that are present in certain tissues or biological fluids only under particular conditions, without even requiring that cDNA libraries be constructed. In one embodiment, the Counter-SELEX process is performed using 1) a first tissue or biological fluid as a SELEX target; and 2) a second tissue or biological fluid as a Counter-SELEX target; those nucleic acid ligands with affinity to the Counter-SELEX target are discarded. Nucleic acid ligands will thereby be obtained that bind to those components of the first tissue or biological fluid that are not present in the second tissue or biological fluid. Alternatively, Counter-SELEX can be performed using: 1) a tissue or biological fluid obtained under a first predetermined condition as a SELEX target; and 2) the same tissue or biological fluid obtained under a second predetermined condition as a Counter-SELEX target. This process will yield nucleic acid ligands to components of the tissue or biological fluid that are present under the first predetermined condition but not under the second predetermined condition. For example, if the predetermined conditions represent different points in a drug administration scheme, then nucleic acid ligands with affinity to drug-responsive components of the tissue or biological fluid can be obtained. Similarly, the predetermined conditions can represent healthy and diseased states of a tissue. Targets of the nucleic acid ligands obtained in these embodiments can be identified through a number of techniques well known in the art e.g., cDNA expression library screening (including "panning" of phage display libraries) or affinity purification.

In yet further embodiments, an in vitro expression system is used to produce a protein target(s) (or fragments thereof, including peptides) for which at least a partial cDNA or genomic sequence is known. In vitro expression systems are well known in the art, and generally perform both the transcription of a sequence of interest, followed by translation of the resulting transcripts. Proteins expressed in vitro can be used as a target for a predetermined number of rounds of the SELEX process. Following a predetermined number of rounds of the SELEX process, the resulting enriched candidate mixture can optionally be used to perform an additional number of rounds of the SELEX process using, as a target, a complex mixture suspected of containing the protein target(s) of interest. Alternatively, an in vitro expression system can be used to translate all of the mRNA molecules expressed in a tissue or biological fluid; then, the SELEX process is performed using the translation products as the target. Finally, an additional number of rounds of the SELEX process can be performed using, as a target, the same tissue or biological fluid from which the mRNA was obtained.

It will be appreciated by those skilled in the art that further variations on this basic scheme using in vitro expression are possible. For example, the Counter-SELEX process can be used in concert with in vitro expression systems in order to generate nucleic acid ligands to protein targets that are expressed in: one tissue but not in another; or, in a diseased tissue (e.g., a tumor), but not in healthy tissue; or in a tissue in response to drug administration. In each case, one in vitro expression system is used to generate SELEX process targets (e.g., in vitro expression of mRNA from tissue A), and a second in vitro expression system is used to generate Counter-SELEX process targets (e.g., in vitro expression of mRNA from tissue B). Finally, in each case the resulting enriched candidate mixture can optionally be further enriched by performing an additional number of rounds of the SELEX process using the appropriate complex mixture as a SELEX target.

D. Uses of the Nucleic Acid Ligands Provided by the Methods of the Instant Invention Nucleic acid ligands identified according to the methods provided herein will have great utility in the field of biomedicine, including, but not limited to, use as diagnostic and prognostic reagents, as reagents for the discovery of novel therapeutics, as reagents for monitoring drug response in individuals, and as reagents for the discovery of novel therapeutic targets. It is expressly contemplated that the methods of the instant invention will provide nucleic acid ligands that can be used in a microarray format, as described in the aforementioned biochip applications.

The methods provided herein may be automated to allow the high-throughput generation of nucleic acid ligands with little operator intervention. Methods and apparatus for the automation of the SELEX process are provided by the aforementioned automated SELEX process applications.

What is claimed is:

1. A method for generating nucleic acid ligands to components of a biological tissue or fluid present under a first predetermined condition and not present under a second predetermined condition, comprising:
   a) providing a peptide, said peptide comprising a linear amino acid sequence identical to at least a portion of a protein suspected of being a component of said biological tissue or fluid obtained under said first predetermined condition;
   b) providing a candidate mixture of nucleic acids;
   c) contacting the candidate mixture of nucleic acids with said peptide, wherein nucleic acids having an increased affinity to said peptide relative to the candidate mixture may be partitioned from the remainder of the candidate mixture;
   d) partitioning the increased affinity nucleic acids from the remainder of the candidate mixture;
   e) amplifying the increased affinity nucleic acids to yield a candidate mixture of nucleic acids enriched for nucleic acids with relatively higher affinity and specificity for said peptide, whereby nucleic acids having a relatively higher affinity for said biological tissue or fluid obtained under said first predetermined condition are generated;

f) contacting said enriched candidate mixture with said biological tissue or fluid obtained under said first predetermined condition, wherein nucleic acids having an increased affinity to components of said biological tissue or fluid present under said first predetermined condition relative to the candidate mixture may be partitioned from the remainder of the candidate mixture;

g) partitioning the increased affinity nucleic acids from the remainder of the candidate mixture;

h) contacting the increased affinity nucleic acids with said biological tissue or fluid obtained under said second predetermined condition, wherein nucleic acids with affinity to components of said biological tissue or fluid present under a second predetermined condition are removed from said increased affinity nucleic acids, whereby nucleic nucleic acids having a relatively higher affinity for said biological tissue or fluid obtained under said first predetermined condition and depleted for nucleic acids with relatively higher affinity and specificity for components of said biological tissue or fluid present under said second predetermined condition are generated; and i) amplifying the nucleic acids retained in step h); whereby nucleic acid ligands to components of said biological tissue or fluid present under said first predetermined condition and not present under said second predetermined condition may be identified.

2. The method of claim 1, wherein the increased affinity nucleic acids of step e) are further enriched for nucleic acids with relatively higher affinity and specificity for said peptide by performing after step e) the steps of:

I) contacting said enriched candidate mixture with said peptide, wherein nucleic acids having an increased affinity to said peptide relative to the enriched candidate mixture may be partitioned from the remainder of the enriched candidate mixture;

II) partitioning the increased affinity nucleic acids from the remainder of the candidate mixture; and III) amplifying the increased affinity nucleic acids to yield a candidate mixture of nucleic acids enriched for nucleic acids with relatively higher affinity and specificity for said peptide;

whereby the increased affinity nucleic acids of step e) are further enriched for nucleic acids with relatively higher affinity and specificity for said peptide, and whereby nucleic acids having a relatively higher affinity for said biological tissue or fluid obtained under said first predetermined condition are generated.

3. A method for generating nucleic acid ligands to components of a biological tissue or fluid present at a first time point and not present at a second time point, comprising:

a) providing a peptide, said peptide comprising a linear amino acid sequence identical to at least a portion of a protein suspected of being a component of said biological tissue or fluid present at said first time point;

b) providing a candidate mixture of nucleic acids;

c) contacting the candidate mixture of nucleic acids with said peptide, wherein nucleic acids having an increased affinity to said peptide relative to the candidate mixture may be partitioned from the remainder of the candidate mixture;

d) partitioning the increased affinity nucleic acids from the remainder of the candidate mixture;

e) amplifying the increased affinity nucleic acids to yield a candidate mixture of nucleic acids enriched for nucleic acids with relatively higher affinity and specificity for said peptide, whereby nucleic acids having a relatively higher affinity for said biological tissue or fluid present at said first time point are generated;

f) providing said biological tissue or fluid obtained at said first time point;

g) contacting the enriched candidate mixture of nucleic acids with said biological tissue or fluid obtained at said first time point, wherein nucleic acids having an increased affinity to components of said biological tissue or fluid present at said first time point relative to the candidate mixture may be partitioned from the remainder of the enriched candidate mixture;

h) partitioning the increased affinity nucleic acids from the remainder of the enriched candidate mixture;

i) contacting the increased affinity nucleic acids with said biological tissue or fluid obtained at said second time point, wherein nucleic acids with affinity to components of said biological tissue or fluid present at said second time point are removed from said increased affinity nucleic acids;

j) amplifying the nucleic acids retained in step i) to yield a candidate mixture of nucleic acids enriched for nucleic acids with relatively higher affinity and specificity for components of said biological tissue or fluid present at said first time point and depleted for nucleic acids with relatively higher affinity and specificity for components of said biological tissue or fluid present at said second time point; whereby nucleic acid ligands to components of said biological tissue or fluid obtained at said first time point and not present at a second time point may be identified.

4. The method of claim 3 wherein said first and said second time points correspond to different time points in a drug administration scheme.

5. A method for generating nucleic acid ligands to a target protein, comprising:

a) providing a peptide, said peptide comprising a linear amino acid sequence identical to at least a portion of a target protein suspected of being expressed by cells;

b) providing a candidate mixture of nucleic acids;

c) contacting the candidate mixture of nucleic acids with said peptide, wherein nucleic acids having an increased affinity to said peptide relative to the candidate mixture may be partitioned from the remainder of the candidate mixture;

d) partitioning the increased affinity nucleic acids from the remainder of the candidate mixture;

e) amplifying the increased affinity nucleic acids to yield a candidate mixture of nucleic acids enriched for nucleic acids with relatively higher affinity and specificity for said peptide, whereby nucleic acids having a relatively higher affinity for said target protein are generated;

f) contacting a medium with cells expressing said target protein, said medium being free of serum and said target protein, to generate a first medium;

g) contacting said enriched candidate mixture of nucleic acids with said first medium, wherein nucleic acids having an increased affinity to said first medium relative to the enriched candidate mixture may be partitioned from the remainder of the enriched candidate mixture;

h) partitioning the increased affinity nucleic acids from the remainder of the enriched candidate mixture;

i) contacting a medium with cells not expressing said target protein, said medium being free of serum and said target protein, to generate a second medium;

j) contacting the increased affinity nucleic acids with said second medium, wherein nucleic acids with affinity to said second medium are removed from said increased affinity nucleic acids;

k) amplifying the nucleic acids retained in step j) to yield a candidate mixture of nucleic acids enriched for nucleic acids with relatively higher affinity and specificity for said target protein and depleted of nucleic acids with relatively higher affinity and specificity for said second medium;

whereby a nucleic acid ligand of said target protein may be identified.

* * * * *